United States Patent [19]

Yamamura et al.

[11] Patent Number: 5,354,936
[45] Date of Patent: Oct. 11, 1994

[54] METHOD FOR PREPARING ETHANE AND ETHYLENE FROM METHANE

[75] Inventors: Masami Yamamura, Kasukabe; Hideo Okado, Ushiku; Naohide Tsuzuki, Noda; Kazutoshi Chaki, Ichihara; Toshiya Wakatsuki, Chiba, all of Japan

[73] Assignee: Sekiyushigen Kaihatsu Kabushiki Kaisha, Tokyo, Japan

[21] Appl. No.: 37,763

[22] Filed: Mar. 26, 1993

[30] Foreign Application Priority Data

Apr. 9, 1992 [JP] Japan ................................ 4-115166

[51] Int. Cl.$^5$ ................................................ C07C 2/00
[52] U.S. Cl. .................................... 585/500; 585/700; 585/943; 585/654; 585/656; 585/658; 585/520
[58] Field of Search ............... 585/500, 700, 943, 654, 585/656, 658, 520

[56] References Cited

U.S. PATENT DOCUMENTS 5,093,542  3/1992  Gaffney ........................... 585/500

Primary Examiner—Anthony McFarlane
Assistant Examiner—E. D. Irzinski
Attorney, Agent, or Firm—Joseph C. Mason, Jr.; Ronald E. Smith

[57] ABSTRACT

A method for preparing ethane and ethylene by reacting methane or a methane-containing natural gas in the presence of oxygen or an oxygen-containing gas, i.e., by partially oxidizing, at a temperature of 500° through 1000° C. using shellfishes or shells as a catalyst is disclosed. The oxidation coupling reaction of methane is controlled so as to remarkably increase the conversion ratio of methane and the selectivity of $C_2^+$ compounds. The waste matter abundantly released from food industries as well as easily accessible natural resources is used as a raw material of a catalyst for the reaction. The present method is extremely useful from the viewpoint of the recycling of waste as well.

5 Claims, No Drawings

METHOD FOR PREPARING ETHANE AND ETHYLENE FROM METHANE

BACKGROUND OF THE INVENTION

1. Field of the Invention

This invention relates to a method for preparing ethane and ethylene by reacting methane or a methane-containing natural gas in the presence of oxygen or an oxygen-containing gas.

2. Description of the Prior Art

Methane is one of the resources which are abundant in the world as a main component of natural gases. However, since methane has low reactivity, the greater part of methane is exhausted as a fuel, and the utilized methods as a raw material for chemical industries are available on a limited basis. In 1982, however, Keller and Virgin reported that ethane and ethylene are produced by partially oxidizing methane using various metal oxides as a catalyst in the presence of oxygen (Journal of Catalysis published in U.S.A. Vol. 73, pp. 9-19, 1982).

Since then, many reports have been made on the useful catalysts for this reaction, which is called as an oxidation coupling reaction for methane. In case of classifying these catalysts, alkali metals and alkaline-earth metals, and for example, rare-earth metals such as lanthanide or their combinations are used as these catalysts in the majority of these catalysts. In particular, there are many reports on the catalysts which mainly consist of alkaline-earth metal. For instance, it is disclosed in Japanese Pat. Laid-open No. 62-267243 that ethane and ethylene are produced using a catalyst of an alkaline-earth metal compound such as calcium oxide.

In most of the above cases, however, the conversion ratio of methane and the selectivity of $C_2$ hydrocarbon in the product are still low and the abilities are not so high as a practical catalyst. Therefore, it is desired to develop the catalysts having more activity and high selectively.

SUMMARY OF THE INVENTION

It is a primary object of the present invention to provide a method for preparing ethane and ethylene using accessible catalysts for further developing the activity and selectivity.

It is another object of the present invention to allow the conversion ratio of methane and the selectivity of a $C_2+$ compound to remarkably increase in the oxidation coupling reaction of methane by reacting methane or a methane-containing natural gas in the presence of oxygen or an oxygen-containing gas, i.e., by partially oxidizing, using shellfishes or shells as a catalyst at a temperature of 500° to 1000° C.

DETAILED DESCRIPTION OF THE PREFERRED EMBODIMENTS

The present inventors have variously examined the catalysts for the oxidation coupling of methane and found that hydrocarbons with two or more carbon atoms such as ethane, ethylene can be prepared at a high activity and a high selectivity by using shellfishes or shells as a catalyst. On the basis of these findings, the present invention has, accordingly, been completed.

The present invention relates to a method for preparing ethane and ethylene by partially oxidizing methane or a methane-containing natural gas with oxygen or an oxygen-containing gas in the presence of shellfishes or shells at a temperature of 500° to 1000° C.

In the present invention, shellfishes or shells are used as a catalyst. The main component of shells is calcium carbonate and contains inorganic salts such as strontium, sodium, magnesium, sulfur or the like, and 1% of a protein called as a conchiolin. The outermost portion of the shells is covered with thin shell layers, the intermediate portion has prismatic layers and the innermost portion has mother of pearl layer. Furthermore, numberless fine capillaries are opened perpendicular to the shell surfaces.

The catalysts to be used in the present invention are usually prepared in the following. Namely, they are prepared by putting shellfishes or shells in an aluminum crucible and by baking at 500° to 1300° C., preferably 600° to 1100° C. and more preferably 700° to 1000° C. It is also possible to prepare the catalysts by baking at 500° to 1300° C. likewise after pulverization.

When the baking temperature is set at not more than 500° C., the selectivity falls. On the other hand, when the baking temperature is set at not less than 1300° C., the activity falls. Therefore, it is necessary to set the baking temperature in a range from 500° to 1300° C. In the catalysts of shellfishes or shells, it is considered that a fine pore structure is formed by baking and that this structure contributes to the manifestation of the high efficiency. It is considered that this fine pore structure is formed by baking while conchiolin in shells, three layer structure of shell layer, prismatic layer and mother of pearl layer, and numberless fine capillaries are referred complicatedly to one another. Therefore, the baking temperature is extremely important to the formation of the fine pore structure.

The catalysts thus obtained are crushed into powder having a size of not less than 100 mesh, which can also be used. However, the catalysts are molded by a compacting molding machine depending on the necessity and then, the catalysts are further crushed into granules with a size of preferably 16 to 32 mesh, which can also be used. Furthermore, these catalysts can also be used with silica sand, alumina, magnesia, calcia, and other diluents.

In addition, one or more kinds of elements selected from a group consisting of alkali metals, metals of Group IIa, metals of Group IIIa, metals of Group IVa, metals of Group Va and metals of Group VIIIa in the periodic table can be used by adding to shellfishes or shells. The salts, oxides and hydroxides of these elements can be used by adding to shellfishes or shells.

In case of conducting the oxidation coupling reaction of methane by utilizing the above catalysts, methane and oxygen are used by mixing methane with oxygen at the mole ratio of $CH_4/O_2$ of 1 to 100, preferably 2 to 70 and more preferably 3 to 50. It is of course justified to allow the catalysts to coexist with an inert gas such as helium, argon and nitrogen as a diluent. These mixed gases are supplied to a reaction tube packed with the catalysts and the reaction is conducted at a temperature of normally 500° to 1000° C., more preferably 600° to 900° C. or most preferably 700° to 850° C. The reaction is normally conducted under atmospheric pressure, but it may, if necessary, be conducted under reduced or compressed pressure as well.

Methane separated from natural gases is usually used in the reaction described above, but methane produced from coal and other materials may be utilized. Furthermore, methane-containing natural gases themselves can also be used as a raw material. Oxygen separated from air by low temperature processing and oxygen concentrated by means of gas separation membranes can be used. Furthermore, oxygen in the air can also be used as it is.

In the case of executing the present invention, the catalysts can be used in any modes of fixed bed, moving bed and fluidized bed.

On the basis of the following examples, further detailed description will be given. However, it is to be understood that other forms might be adopted. In addition, shells may be used instead of shellfishes, and the shellfishes including the contents may be used as they are.

Results in Examples 1 to 7 are given in Tables 1 and 2 respectively and those in Comparative Examples 1 to 4 are given in Table 3.

EXAMPLE 1

(1) Preparation of Catalysts

Corbiculas were put in an alumina-made crucible, dried at 120° C. and baked at 900° C. for 10 hours.

(2) Reaction Test

After 1 g of the above catalyst was packed in an alumina-made reaction tube, mixed gas of methane and oxygen in the ratio of 9:1 was passed through the reaction tube at a flow rate of 100 ml/min at temperatures of 750° C. and 800° C. under atmospheric pressure to react the mixed gas.

The reaction products prepared by the procedure described above were introduced into a gas chromatograph column using a sampling loop attached to the outlet of the reaction tube and then analyzed. The analytical results thus obtained are given in Table 1. In Table 1, methane and oxygen conversion ratios represent the proportion of the reacted methane and oxygen and $C_2^+$ selectivity represents the composition ratio of the hydrocarbons of two or more carbon atoms in the reaction products.

EXAMPLE 2

Following the procedure described in Example 1 except the use of clams instead of corbiculas, the catalyst was prepared and then the reaction was conducted. The results thus obtained are shown in Table 1.

EXAMPLE 3

Following the procedure described in Example 1 except the use of trough shells instead of corbiculas, the catalyst was prepared and then the reaction was conducted. The results thus obtained are shown in Table 1.

EXAMPLE 4

Following the procedure described in Example 1 except the use of hard-shelled mussels instead of corbiculas, the catalyst was prepared and then the reaction was conducted. The results thus obtained are shown in Table 1.

TABLE 1

| Catalyst | | Temp. (°C.) | Conversion Ratio (%) CH$_4$ | O$_2$ | Selectivity (%) C$_2^+$ |
|---|---|---|---|---|---|
| Example 1 | corbicula | 750 | 14.8 | 94.8 | 85.2 |
| | | 800 | 14.7 | 94.4 | 84.8 |
| Example 2 | clam | 750 | 17.7 | 97.8 | 79.2 |
| | | 800 | 17.4 | 98.3 | 79.1 |
| Example 3 | trough shell | 750 | 15.1 | 90.3 | 77.4 |
| | | 800 | 15.9 | 97.0 | 78.5 |

TABLE 1-continued

| Catalyst | | Temp. (°C.) | Conversion Ratio (%) CH$_4$ | O$_2$ | Selectivity (%) C$_2^+$ |
|---|---|---|---|---|---|
| Example 4 | hard-shelled mussel | 750 | 16.2 | 97.8 | 77.5 |
| | | 800 | 16.6 | 98.1 | 78.5 |

Reaction condition:

CH$_4$:O$_2$=9:1 (mole ratio), total gas supply: 100 ml/min and catalyst amount: 1 g

EXAMPLE 5

Following the procedure described in Example 1 except the use of scallops instead of corbiculas, the catalyst was prepared and then the reaction was conducted. The results thus obtained are shown in Table 2.

EXAMPLE 6

Following the procedure described in Example 1 except the use of periwinkles instead of corbiculas, the catalyst was prepared and then the reaction was conducted. The results thus obtained are shown in Table 2.

EXAMPLE 7

Following the procedure described in Example 1 except the use of ark shells instead of corbiculas, the catalyst was prepared and then the reaction was conducted. The results thus obtained are shown in Table 2.

TABLE 2

| Catalyst | | Temp. (°C.) | Conversion Ratio (%) CH$_4$ | O$_2$ | Selectivity (%) C$_2^+$ |
|---|---|---|---|---|---|
| Example 5 | scallop | 750 | 17.8 | 96.2 | 81.1 |
| | | 800 | 17.5 | 98.2 | 80.4 |
| Example 6 | periwinkle | 750 | 16.8 | 83.7 | 79.8 |
| | | 800 | 17.6 | 96.7 | 82.4 |
| Example 7 | ark shell | 750 | 16.7 | 97.8 | 78.3 |
| | | 800 | 16.5 | 98.3 | 77.2 |

Reaction condition:

CH$_4$:O$_2$=9:1 (mole ratio), total gas supply: 100 ml/min and catalyst amount: 1 g

COMPARATIVE EXAMPLE 1

Following the procedure described in Example 1 except the use of calcium oxide instead of corbiculas, the catalyst was prepared and then the reaction was conducted. The results thus obtained are shown in Table 3.

COMPARATIVE EXAMPLE 2

Following the procedure described in Example 1 except the use of calcium carbonate instead of corbiculas, the catalyst was prepared and then the reaction was conducted. The results thus obtained are shown in Table 3.

COMPARATIVE EXAMPLE 3

Following the procedure described in Example 1 by use of corbiculas and except heating them at 1300° C., the catalyst was prepared and then the reaction was conducted. The results thus obtained are shown in Table 3.

COMPARATIVE EXAMPLE 4

Following the procedure described in Example 1 by use of corbiculas and except heating them at 1700° C., the catalyst was prepared and then the reaction was conducted. The results thus obtained are shown in Table 3.

TABLE 3

| Catalyst | | Temp. (°C.) | Conversion Ratio (%) | | Selectivity (%) $C_2^+$ |
| --- | --- | --- | --- | --- | --- |
| | | | $CH_4$ | $O_2$ | |
| Comparative example 1 | Calcium oxide | 750 | 9.9 | 95.2 | 40.1 |
| | | 800 | 11.9 | 98.0 | 55.1 |
| Comparative example 2 | Calcium carbonate | 750 | 9.0 | 97.5 | 48.1 |
| | | 800 | 10.7 | 98.9 | 60.8 |
| Comparative example 3 | Corbicula (baking at 1300° C.) | 750 | 8.5 | 64.6 | 60.5 |
| | | 800 | 12.4 | 94.4 | 64.8 |
| Comparative example 4 | Corbicula (baking at 1700° C.) | 750 | 1.6 | 16.9 | 30.8 |
| | | 800 | 6.1 | 85.2 | 39.7 |

Reaction condition:
$CH_4:O_2 = 9:1$ (mole ratio), total gas supply: 100 ml/min and catalyst amount: 1 g

What is claimed is:

1. Method for the partial oxidation of methane which comprises contacting methane with oxygen under effective reaction conditions and in the presence of a solid catalyst comprising a product formed by subjecting shellfish or its shell to a temperature from 500° C. to 1300° C. whereby an oxidation product containing two or more carbon atoms is obtained.

2. Method according to claim 1 wherein the shellfish or its shell are corbiculas, clams, or scallops and the oxidation product comprises ethane and ethylene.

3. Method according to claim 1 wherein the reaction conditions include a temperature of 500° C. to 1000° C., and a mole ratio of $CH_4/O_2$ from 1 to 100.

4. A catalytic method of, converting, in a catalytic mode under oxygen partial pressure, methane by partial oxidation to yield a hydrocarbon product containing two or more carbon atoms wherein the catalytic method is carried out under effective conversion reaction conditions and in the presence of a catalyst containing the product obtained by subjecting shellfish or its shell to a temperature form 500° C. to 1300° C., and wherein the catalytic method of conversion takes place at a temperature from 500° C. to 1000° C.

5. A catalytic method according to claim 4 wherein the catalyst comprises the shells from corbiculas, clams, or scallops and the hydrocarbon product comprises ethane and ethylene.

* * * * *